US008461968B2

(12) United States Patent  
Ball et al.

(10) Patent No.: US 8,461,968 B2  
(45) Date of Patent: Jun. 11, 2013

(54) MATTRESS FOR A HOSPITAL BED FOR USE IN A HEALTHCARE FACILITY AND MANAGEMENT OF SAME

(75) Inventors: David E. Ball, Mt. Pleasant, SC (US); Richard B. Stacy, Daniel Island, SC (US)

(73) Assignee: Hill-Rom Services, Inc., Batesville, IN (US)

( * ) Notice: Subject to any disclaimer, the term of this patent is extended or adjusted under 35 U.S.C. 154(b) by 1097 days.

(21) Appl. No.: 11/846,889

(22) Filed: Aug. 29, 2007

(65) Prior Publication Data

US 2009/0056027 A1   Mar. 5, 2009

(51) Int. Cl.
*G09F 25/00* (2006.01)
*A47C 17/00* (2006.01)

(52) U.S. Cl.
USPC .......................................... 340/286.02; 5/690

(58) Field of Classification Search
USPC ........................................... 340/286.02, 10.1
See application file for complete search history.

(56) References Cited

U.S. PATENT DOCUMENTS

| | | |
|---|---|---|
| 2,330,356 A | 9/1943 | Belliveau |
| 2,335,524 A | 11/1943 | Lomax |
| 2,736,888 A | 2/1956 | McLain |
| 2,896,021 A | 7/1959 | Philipps |
| 3,098,220 A | 7/1963 | De Graaf |
| 3,439,320 A | 4/1969 | Ward |
| 3,478,344 A | 11/1969 | Schwitzgebel et al. |
| 3,553,383 A | 1/1971 | Rochtus |
| 3,599,199 A | 8/1971 | Bunting |
| 3,599,200 A | 8/1971 | Bunting |
| 3,696,384 A | 10/1972 | Lester |
| 3,739,329 A | 6/1973 | Lester |
| 3,767,859 A | 10/1973 | Doering et al. |
| 3,805,265 A | 4/1974 | Lester |
| 3,913,153 A | 10/1975 | Adams et al. |
| 3,973,200 A | 8/1976 | Akerberg |
| 4,067,005 A | 1/1978 | Levy et al. |
| 4,150,284 A | 4/1979 | Trenkler et al. |
| 4,151,407 A | 4/1979 | McBride et al. |
| 4,183,015 A | 1/1980 | Drew et al. |
| 4,216,462 A | 8/1980 | McGrath et al. |
| 4,225,953 A | 9/1980 | Simon et al. |
| 4,228,426 A | 10/1980 | Roberts |
| 4,237,344 A | 12/1980 | Moore |
| 4,264,982 A | 4/1981 | Sakarya |
| 4,275,385 A | 6/1981 | White |
| 4,279,433 A | 7/1981 | Petaja |
| 4,298,863 A | 11/1981 | Natitus et al. |
| 4,331,953 A | 5/1982 | Blevins et al. |
| 4,356,475 A | 10/1982 | Neumann et al. |
| 4,418,334 A | 11/1983 | Burnett |
| 4,455,548 A | 6/1984 | Burnett |
| 4,489,387 A | 12/1984 | Lamb et al. |
| 4,495,495 A | 1/1985 | Ormanns et al. |

(Continued)

FOREIGN PATENT DOCUMENTS

WO   WO 02/091297 A1   11/2002
WO   WO 2004/036390 A2   4/2004

*Primary Examiner* — Benjamin C. Lee
*Assistant Examiner* — Cal Eustaquio
(74) *Attorney, Agent, or Firm* — Barnes & Thornburg LLP

(57) ABSTRACT

A mattress or support surface including an identifier to enable the mattress or support surface to be associated with a location in the healthcare facility and more particularly a room within the healthcare facility.

24 Claims, 7 Drawing Sheets

U.S. PATENT DOCUMENTS

| | | |
|---|---|---|
| 4,495,496 A | 1/1985 | Miller, III |
| 4,539,560 A | 9/1985 | Fleck et al. |
| 4,577,185 A | 3/1986 | Andersen |
| 4,578,671 A | 3/1986 | Flowers |
| 4,582,280 A | 4/1986 | Nichols et al. |
| 4,593,273 A | 6/1986 | Narcisse |
| 4,598,275 A | 7/1986 | Ross et al. |
| 4,601,064 A | 7/1986 | Shipley |
| 4,649,385 A | 3/1987 | Aires et al. |
| 4,680,790 A | 7/1987 | Packard et al. |
| 4,709,330 A | 11/1987 | Yokoi et al. |
| 4,740,788 A | 4/1988 | Konneker |
| 4,752,951 A | 6/1988 | Konneker |
| 4,792,798 A | 12/1988 | Wilowski |
| 4,795,905 A | 1/1989 | Zierhut |
| 4,814,751 A | 3/1989 | Hawkins et al. |
| 4,833,452 A | 5/1989 | Currier |
| 4,833,467 A | 5/1989 | Kobayashi et al. |
| 4,837,568 A | 6/1989 | Snaper |
| 4,853,692 A | 8/1989 | Wolk et al. |
| 4,899,135 A | 2/1990 | Ghahariiran |
| 4,947,152 A | 8/1990 | Hodges |
| 4,955,000 A | 9/1990 | Nastrom |
| 4,967,195 A | 10/1990 | Shipley |
| 4,990,892 A | 2/1991 | Guest et al. |
| 4,998,095 A | 3/1991 | Shields |
| 4,998,939 A | 3/1991 | Potthast et al. |
| 5,006,830 A | 4/1991 | Merritt |
| 5,027,314 A | 6/1991 | Linwood et al. |
| 5,041,086 A | 8/1991 | Koenig et al. |
| 5,062,151 A | 10/1991 | Shipley |
| 5,065,154 A | 11/1991 | Kaiser et al. |
| 5,086,290 A | 2/1992 | Murray et al. |
| 5,103,108 A | 4/1992 | Crimmins |
| 5,124,991 A | 6/1992 | Allen |
| 5,137,033 A | 8/1992 | Norton |
| 5,153,584 A | 10/1992 | Engira |
| 5,266,944 A | 11/1993 | Carroll et al. |
| 5,291,399 A | 3/1994 | Chaco |
| 5,319,355 A | 6/1994 | Russek |
| 5,319,363 A | 6/1994 | Welch et al. |
| 5,357,254 A | 10/1994 | Kah, Jr. |
| 5,375,604 A | 12/1994 | Kelly et al. |
| 5,396,224 A | 3/1995 | Dukes et al. |
| 5,396,227 A | 3/1995 | Carroll et al. |
| 5,416,695 A | 5/1995 | Stutman et al. |
| 5,434,775 A | 7/1995 | Sims et al. |
| 5,446,678 A | 8/1995 | Saltzstein et al. |
| 5,455,560 A | 10/1995 | Owen |
| 5,458,123 A | 10/1995 | Unger |
| 5,461,390 A | 10/1995 | Hoshen |
| 5,475,367 A | 12/1995 | Prevost |
| 5,534,851 A | 7/1996 | Russek |
| 5,537,459 A | 7/1996 | Price et al. |
| 5,548,637 A | 8/1996 | Heller et al. |
| 5,549,113 A | 8/1996 | Halleck et al. |
| 5,561,412 A | 10/1996 | Novak et al. |
| 5,568,119 A | 10/1996 | Schipper et al. |
| 5,576,952 A | 11/1996 | Stutman et al. |
| 5,579,001 A | 11/1996 | Dempsey et al. |
| 5,588,005 A | 12/1996 | Ali et al. |
| 5,594,786 A | 1/1997 | Chaco et al. |
| 5,621,388 A | 4/1997 | Sherburne et al. |
| 5,635,907 A | 6/1997 | Bernard et al. |
| 5,636,245 A | 6/1997 | Ernst et al. |
| 5,640,953 A | 6/1997 | Bishop et al. |
| 5,650,769 A | 7/1997 | Campana, Jr. |
| 5,650,770 A | 7/1997 | Schlager et al. |
| 5,664,270 A | 9/1997 | Bell et al. |
| 5,682,139 A | 10/1997 | Pradeep et al. |
| 5,686,888 A | 11/1997 | Welles, II et al. |
| 5,686,902 A | 11/1997 | Reis et al. |
| 5,687,734 A | 11/1997 | Dempsey et al. |
| 5,689,229 A | 11/1997 | Chaco et al. |
| 5,691,980 A | 11/1997 | Welles, II et al. |
| 5,699,038 A | 12/1997 | Ulrich et al. |
| 5,705,980 A | 1/1998 | Shapiro |
| 5,708,421 A | 1/1998 | Boyd |
| 5,713,856 A | 2/1998 | Eggers et al. |
| 5,719,761 A | 2/1998 | Gatti et al. |
| 5,731,757 A | 3/1998 | Layson, Jr. |
| 5,742,237 A | 4/1998 | Bledsoe |
| 5,751,246 A | 5/1998 | Hertel |
| 5,752,917 A | 5/1998 | Fuchs |
| 5,760,704 A | 6/1998 | Barton et al. |
| 5,767,791 A | 6/1998 | Stoop et al. |
| 5,781,442 A | 7/1998 | Engleson et al. |
| 5,793,290 A | 8/1998 | Eagleson et al. |
| 5,808,564 A | 9/1998 | Simms et al. |
| 5,812,056 A | 9/1998 | Law |
| 5,822,418 A | 10/1998 | Yacenda et al. |
| 5,822,544 A | 10/1998 | Chaco et al. |
| 5,838,223 A | 11/1998 | Gallant et al. |
| 5,844,488 A | 12/1998 | Musick |
| 5,867,821 A | 2/1999 | Ballantyne et al. |
| 5,877,675 A | 3/1999 | Rebstock et al. |
| 5,933,488 A | 8/1999 | Marcus et al. |
| 5,936,539 A | 8/1999 | Fuchs |
| 5,942,986 A | 8/1999 | Shabot et al. |
| 5,944,659 A | 8/1999 | Flach et al. |
| 5,963,137 A | 10/1999 | Waters, Sr. |
| 5,974,389 A | 10/1999 | Clark et al. |
| 5,991,728 A | 11/1999 | DeBusk et al. |
| 5,995,937 A | 11/1999 | DeBusk et al. |
| 6,014,633 A | 1/2000 | DeBusk et al. |
| 6,057,758 A | 5/2000 | Dempsey et al. |
| 6,057,782 A | 5/2000 | Koenig |
| 6,067,019 A | 5/2000 | Scott |
| 6,076,166 A | 6/2000 | Moshfeghi et al. |
| 6,085,493 A | 7/2000 | DeBusk et al. |
| 6,088,362 A | 7/2000 | Turnbull et al. |
| 6,093,146 A | 7/2000 | Filangeri |
| 6,097,308 A | 8/2000 | Albert et al. |
| 6,128,512 A | 10/2000 | Trompower et al. |
| 6,133,837 A | 10/2000 | Riley |
| 6,147,592 A | 11/2000 | Ulrich et al. |
| 6,183,417 B1 | 2/2001 | Geheb et al. |
| 6,208,250 B1 | 3/2001 | Dixon et al. |
| 6,218,942 B1 * | 4/2001 | Vega et al. ................. 340/572.1 |
| 6,241,668 B1 | 6/2001 | Herzog |
| 6,259,355 B1 | 7/2001 | Chaco et al. |
| 6,264,614 B1 | 7/2001 | Albert et al. |
| 6,279,183 B1 | 8/2001 | Kummer et al. |
| 6,287,253 B1 | 9/2001 | Ortega et al. |
| 6,302,844 B1 | 10/2001 | Walker et al. |
| 6,314,556 B1 | 11/2001 | DeBusk et al. |
| 6,320,510 B2 | 11/2001 | Menkedick et al. |
| 6,344,794 B1 | 2/2002 | Ulrich et al. |
| 6,348,777 B1 | 2/2002 | Brown et al. |
| 6,362,725 B1 | 3/2002 | Ulrich et al. |
| 6,364,834 B1 | 4/2002 | Reuss et al. |
| 6,398,727 B1 | 6/2002 | Bui et al. |
| 6,406,426 B1 | 6/2002 | Reuss et al. |
| 6,407,335 B1 | 6/2002 | Franklin-Lees et al. |
| 6,412,980 B1 | 7/2002 | Lounsberry et al. |
| 6,416,471 B1 | 7/2002 | Kumar et al. |
| 6,421,649 B1 | 7/2002 | Rattner |
| 6,439,769 B1 | 8/2002 | Polkus et al. |
| 6,441,742 B1 | 8/2002 | Lovely et al. |
| 6,442,290 B1 | 8/2002 | Ellis et al. |
| 6,445,299 B1 | 9/2002 | Rojas, Jr. |
| 6,450,956 B1 | 9/2002 | Rappaport et al. |
| 6,462,656 B2 | 10/2002 | Ulrich et al. |
| 6,486,792 B1 | 11/2002 | Moster et al. |
| 6,493,568 B1 | 12/2002 | Bell et al. |
| 6,494,831 B1 | 12/2002 | Koritzinsky |
| 6,510,344 B1 | 1/2003 | Halpern |
| 6,516,324 B1 | 2/2003 | Jones et al. |
| 6,526,310 B1 | 2/2003 | Carter et al. |
| 6,529,164 B1 | 3/2003 | Carter |
| 6,533,453 B1 | 3/2003 | Heidsieck et al. |
| 6,535,576 B2 | 3/2003 | Vafi et al. |
| 6,539,393 B1 | 3/2003 | Kabala |
| 6,544,173 B2 | 4/2003 | West et al. |
| 6,544,174 B2 | 4/2003 | West et al. |
| 6,551,243 B2 | 4/2003 | Bocionek et al. |
| 6,553,106 B1 | 4/2003 | Gould et al. |

| | | | | | | |
|---|---|---|---|---|---|---|
| 6,554,174 B1 | 4/2003 | Aceves | | 6,832,199 B1 | 12/2004 | Kucek et al. |
| 6,556,630 B1 | 4/2003 | Brinsfield et al. | | 6,840,117 B2 | 1/2005 | Hubbard, Jr. |
| 6,560,274 B1 | 5/2003 | Leitgeb et al. | | 6,847,302 B2 * | 1/2005 | Flanagan et al. ............. 340/666 |
| 6,572,556 B2 | 6/2003 | Stoycos et al. | | 6,847,814 B1 | 1/2005 | Vogeleisen |
| 6,575,901 B2 | 6/2003 | Stoycos et al. | | 6,868,256 B2 | 3/2005 | Dooley et al. |
| 6,581,204 B2 | 6/2003 | DeBusk et al. | | 6,871,211 B2 | 3/2005 | Labounty et al. |
| 6,584,182 B2 | 6/2003 | Brodnick | | 6,873,884 B2 | 3/2005 | Brackett et al. |
| 6,584,454 B1 | 6/2003 | Hummel, Jr. et al. | | 6,876,985 B2 | 4/2005 | Kawanaka |
| 6,585,645 B2 | 7/2003 | Hutchinson | | 6,885,288 B2 | 4/2005 | Pincus |
| 6,589,170 B1 | 7/2003 | Flach et al. | | 6,891,909 B2 | 5/2005 | Hurley et al. |
| 6,593,528 B2 | 7/2003 | Franklin-Lees et al. | | 6,904,161 B1 | 6/2005 | Becker et al. |
| 6,594,146 B2 | 7/2003 | Frangesch et al. | | 6,909,995 B2 | 6/2005 | Shiraishi |
| 6,594,519 B2 | 7/2003 | Stoycos et al. | | 6,912,549 B2 | 6/2005 | Rotter et al. |
| 6,600,421 B2 | 7/2003 | Freeman | | 6,915,170 B2 | 7/2005 | Engleson et al. |
| 6,603,494 B1 | 8/2003 | Banks et al. | | 6,925,367 B2 | 8/2005 | Fontius |
| 6,609,115 B1 | 8/2003 | Mehring et al. | | 6,930,878 B2 | 8/2005 | Brackett et al. |
| 6,616,606 B1 | 9/2003 | Petersen et al. | | 6,987,448 B2 | 1/2006 | Catton et al. |
| 6,622,088 B2 | 9/2003 | Hood | | 7,068,143 B2 | 6/2006 | Doering et al. |
| 6,640,246 B1 | 10/2003 | Gary, Jr. et al. | | 7,464,001 B1 * | 12/2008 | Adams .......................... 702/183 |
| 6,643,238 B2 | 11/2003 | Nakajima | | 7,868,740 B2 | 1/2011 | McNeely et al. |
| 6,650,346 B1 | 11/2003 | Jaeger et al. | | 8,031,057 B2 | 10/2011 | Mcneely et al. |
| 6,659,947 B1 | 12/2003 | Carter et al. | | 2001/0050610 A1 | 12/2001 | Gelston |
| 6,665,385 B2 | 12/2003 | Rogers et al. | | 2001/0051765 A1 | 12/2001 | Walker et al. |
| 6,665,820 B1 | 12/2003 | Frowein et al. | | 2002/0014951 A1 | 2/2002 | Kramer et al. |
| 6,669,630 B1 | 12/2003 | Joliat et al. | | 2002/0044043 A1 | 4/2002 | Chaco et al. |
| 6,671,547 B2 | 12/2003 | Lyster et al. | | 2002/0044059 A1 | 4/2002 | Reeder et al. |
| 6,671,563 B1 | 12/2003 | Engelson et al. | | 2002/0057340 A1 * | 5/2002 | Fernandez et al. ............ 348/143 |
| 6,685,633 B2 | 2/2004 | Albert et al. | | 2002/0067273 A1 | 6/2002 | Jaques et al. |
| 6,689,091 B2 | 2/2004 | Bui et al. | | 2002/0070867 A1 | 6/2002 | Conway et al. |
| 6,694,367 B2 | 2/2004 | Miesbauer et al. | | 2002/0080037 A1 | 6/2002 | Dixon et al. |
| 6,694,509 B1 | 2/2004 | Stoval et al. | | 2002/0103674 A1 | 8/2002 | Reeder et al. |
| 6,697,765 B2 | 2/2004 | Kuth | | 2002/0143320 A1 * | 10/2002 | Levin ................................ 606/1 |
| 6,707,476 B1 | 3/2004 | Hochstedler | | 2002/0151990 A1 | 10/2002 | Ulrich et al. |
| 6,714,913 B2 | 3/2004 | Brandt et al. | | 2002/0173991 A1 | 11/2002 | Avitall |
| 6,721,818 B1 | 4/2004 | Nakamura | | 2002/0186136 A1 | 12/2002 | Schuman |
| 6,726,634 B2 | 4/2004 | Freeman | | 2002/0196141 A1 | 12/2002 | Boone et al. |
| 6,727,818 B1 | 4/2004 | Wildman et al. | | 2003/0010345 A1 | 1/2003 | Koblasz et al. |
| 6,731,311 B2 | 5/2004 | Bufe et al. | | 2003/0028449 A1 | 2/2003 | Heinen et al. |
| 6,731,989 B2 | 5/2004 | Engleson et al. | | 2003/0030569 A1 | 2/2003 | Ulrich et al. |
| 6,740,033 B1 | 5/2004 | Olejniczak et al. | | 2003/0052787 A1 | 3/2003 | Zerhusen et al. |
| 6,749,566 B2 | 6/2004 | Russ | | 2003/0074222 A1 | 4/2003 | Rosow et al. |
| 6,751,630 B1 | 6/2004 | Franks et al. | | 2003/0146835 A1 | 8/2003 | Carter |
| 6,754,545 B2 | 6/2004 | Haeuser et al. | | 2003/0149598 A1 | 8/2003 | Santoso et al. |
| 6,754,883 B2 | 6/2004 | DeBusk et al. | | 2003/0176798 A1 | 9/2003 | Simon |
| 6,759,959 B2 | 7/2004 | Wildman | | 2003/0206116 A1 | 11/2003 | Weiner et al. |
| 6,763,541 B2 | 7/2004 | Mahoney et al. | | 2004/0183681 A1 | 9/2004 | Smith |
| 6,771,172 B1 | 8/2004 | Robinson et al. | | 2004/0183683 A1 * | 9/2004 | Funahashi .................. 340/573.1 |
| 6,773,396 B2 | 8/2004 | Flach et al. | | 2004/0183684 A1 | 9/2004 | Callaway |
| 6,778,225 B2 | 8/2004 | David | | 2004/0186358 A1 | 9/2004 | Chernow et al. |
| 6,781,517 B2 | 8/2004 | Moster et al. | | 2004/0193449 A1 | 9/2004 | Wildman et al. |
| 6,784,797 B2 | 8/2004 | Smith et al. | | 2005/0035862 A1 | 2/2005 | Wildman et al. |
| 6,791,460 B2 | 9/2004 | Dixon et al. | | 2005/0219059 A1 | 10/2005 | Ulrich et al. |
| 6,792,396 B2 | 9/2004 | Inda et al. | | 2005/0242946 A1 | 11/2005 | Hubbard, Jr. et al. |
| 6,801,227 B2 | 10/2004 | Bocionek et al. | | 2006/0279427 A1 | 12/2006 | Becker et al. |
| 6,807,543 B2 | 10/2004 | Muthya | | 2007/0120689 A1 * | 5/2007 | Zerhusen et al. ........... 340/573.1 |
| 6,825,763 B2 | 11/2004 | Ulrich et al. | | 2008/0010752 A1 * | 1/2008 | Chambers et al. ................. 5/706 |
| 6,826,578 B2 | 11/2004 | Brackett et al. | | 2009/0070942 A1 * | 3/2009 | Chambers et al. ................. 5/713 |
| 6,828,992 B1 | 12/2004 | Freeman et al. | | 2012/0013452 A1 | 1/2012 | McNeely et al. |
| 6,829,796 B2 | 12/2004 | Salvatini et al. | | | | |
| 6,830,549 B2 | 12/2004 | Bui et al. | | * cited by examiner | | |

MATTRESS FOR A HOSPITAL BED FOR USE IN A HEALTHCARE FACILITY AND MANAGEMENT OF SAME

BACKGROUND OF THE INVENTION

The present disclosure relates to mattresses for a hospital bed for use in a healthcare facility. More particularly, the present disclosure relates to a mattress or support surface having a unique identifier to identify a location of the mattress within the healthcare facility and more particularly to identify a location of the mattress within a room of the healthcare facility.

Some hospital beds can be configured to communicate information to a nurse call system or to other information systems located within a healthcare facility. Such systems typically include a computer system or other electronic communication system at a nurses station which is remotely located from the hospital bed. The computer system can include a monitor to display information relating to the status of a bed. The hospital bed can include one or more nurse call buttons located on the side rails of the bed and/or on a handheld pendant which is located adjacent to or at the bed. The patient can press one of the buttons to request or to speak to a nurse or other caregiver. In addition, the nurse at the remote station can communicate with the patient with a two-way communications link including audio circuitry such as a microphone and a speaker located either on the bed itself or mounted on equipment or the wall of the room.

Hospital beds which can communicate with such computer systems, typically connect via a wired connection established by a cable that extends between the bed and an interface unit mounted on a wall or a head wall of the hospital room. Such a wired communication cannot only provide for communication between a patient and a caregiver, but also provide bed status information to locations which are remote from the bed. Such bed status information allows medical personnel and other caregivers to monitor the status of the bed including the location of siderails, the position of an articulating deck, and the current status of certain bed components such as brakes not set or bed exit system not armed.

For instance, it is also possible for such a bed status information to provide information unique to a particular bed frame. Identification information can identify the model type of the bed frame, the serial number of the bed frame, and its functional capabilities.

SUMMARY OF THE INVENTION

The present invention may comprise a system, apparatus and/or method that may have one or more of the following features and/or steps, which alone or in any combination may comprise patentable subject matter.

In accordance with one aspect of the disclosed embodiments, there is provided a mattress for use in a healthcare facility having a communications system and a plurality of bed frames. The mattress includes a support member and a unique electronic identifier, associated with the mattress, to uniquely identify the mattress.

In accordance with another aspect of the disclosed embodiments, there is provided a method of determining the location of a mattress within a health care facility having a communication system, a plurality of bed frames, and a plurality of mattresses. The method includes the steps of assigning a unique identifier to each of the plurality of mattresses, placing one of the uniquely identified mattresses on one of the plurality of bed frames, confirming placement of one of the uniquely identified mattresses on the one of the plurality of bed frames, and sending the unique identifier assigned to one of the uniquely identified mattresses over the communication system.

Pursuant to another aspect of the disclosed embodiments, there is provided a system including a communication system, a plurality of uniquely identified mattresses wherein each of the uniquely identified mattresses includes a unique electronic identifier, and a plurality of bed frames. The system may further include an install confirmation device to confirm association of one of the uniquely identified mattresses with one of the bed frames.

Each of the plurality of uniquely identified mattresses includes a support member and a transceiver associated with the mattress. Each of the uniquely identified mattresses may includes a network interface device operably coupled to the transceiver. The transceiver is operably coupled to the communication system to transmit the unique electronic identifier over the communication system. The network interface device is adapted to store the unique electronic identifier. The unique electronic identifier may include an internet protocol address. The transceiver may include a wireless transceiver and the wireless transceiver may be part of the network interface device.

The system may further include a computing device coupled to the communication system to receive and store the unique electronic identifiers from the plurality of uniquely identified mattresses. The computing device may provide an interface to present information regarding the plurality of uniquely identified mattresses. In particular, the interface may present information that identifies each mattress of the plurality of uniquely identified mattresses and that identifies a patient assigned to each mattress of the plurality of uniquely identified mattresses. The interface may also present information that identifies each mattress of the plurality of uniquely identified mattresses, a location of each mattress in the healthcare facility, a type for each mattress, features provided by each mattress, and/or a history of use for each mattress.

DETAILED DESCRIPTION OF THE DRAWINGS

Figure 1:
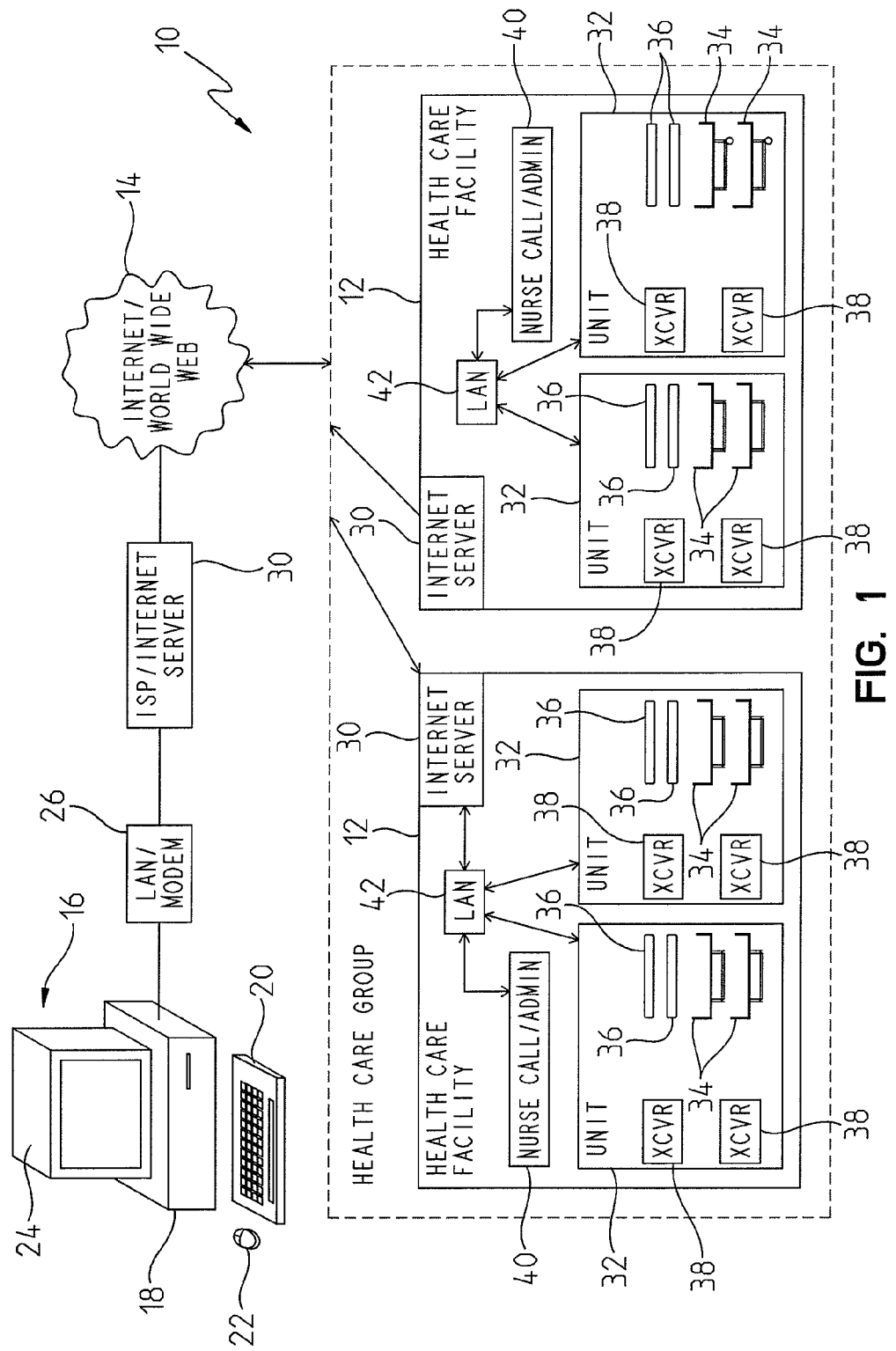
FIG. 1 illustrates a diagrammatic view of a healthcare facility including a plurality of hospital beds having mattresses or support surfaces having a unique identifier to locate the mattress within the healthcare facility.

FIG. 1 illustrates a diagrammatic view of a healthcare group 10 including one or more healthcare facilities 12. Healthcare facilities 12 typically include hospitals, surgery centers, nursing homes, and even private homes which have been adapted or used for in-home healthcare. The healthcare group 10, including the variety of healthcare facilities 12, are coupled to an internet/worldwide web 14, as is understood by those skilled in the art. A computing device 16, such as a personal computer, is also coupled to the internet/worldwide web 14. The computing device 16 includes a computer 18 coupled to a keyboard 20 and a mouse 22. The keyboard 20 and the mouse 22 include user inputs for inputting information or data to the computer 18 and for accessing information or data from the computer 18 as well. A monitor 24, coupled to the computer 18, enables a user to view the information being either input or accessed. The computing system 16 is coupled to a local area network 26 or to a modem 26 which is in turn coupled to the internet/worldwide web 14 an internet server or internet service provider (ISP) 30. While the computing system 16 is indicated as being located away from and outside of the healthcare group 10, such location is merely for illustrative purposes. While the computing system 16 can reside within any numbers of locations, including an individual caregivers home, or a public library, the computing system 16 can also be located within the healthcare group 10 and in particular one of the healthcare facilities 12.

The healthcare group 10 includes one or more healthcare facilities 12 each of which can be coupled to the worldwide web through an internet server 30 located either within the healthcare facility 12 or remotely therefrom. While the description of the present invention includes reference to a healthcare group 10 including one or more healthcare facilities, the present invention is equally applicable to individual healthcare facilities which are not affiliated with a larger healthcare group. Consequently, the internet server which is used by a healthcare facility to communicate with the internet/worldwide web 14 may also be located remotely at an internet service provider, such as is understood by those skilled in the art.

The healthcare facility can include one or more units 32 which typically are devoted primarily to providing a particular or specialized type of healthcare. For instance, one healthcare unit 32 might be particularly devoted to providing cardiac healthcare, while another particular unit 32 might be devoted to providing orthopedic healthcare. Consequently, the present invention is not limited in any way by the type of healthcare provided and can include all types of healthcare.

Each of the healthcare units typically includes a plurality of healthcare beds, each including a frame 34 and a mattress 36. Frames and mattresses are well know in the art. Mattresses include a support member which can include foam, air bladders, or combinations thereof. Each of the mattresses includes a unique electronic identifier. While illustrated here as being separate components, a single mattress is typically associated with a single frame and is adapted to support a patient. The healthcare unit 32 further includes one or more transceivers (xcvr) 38 which can provide communication between the beds and a nurses station 40 through a local area network 42. The nurses station 40 can provide the functions of a nurse call station as well as to provide an administrative station for an administrator to set up the communication/computing/informational system of the present invention.

Figure 2:
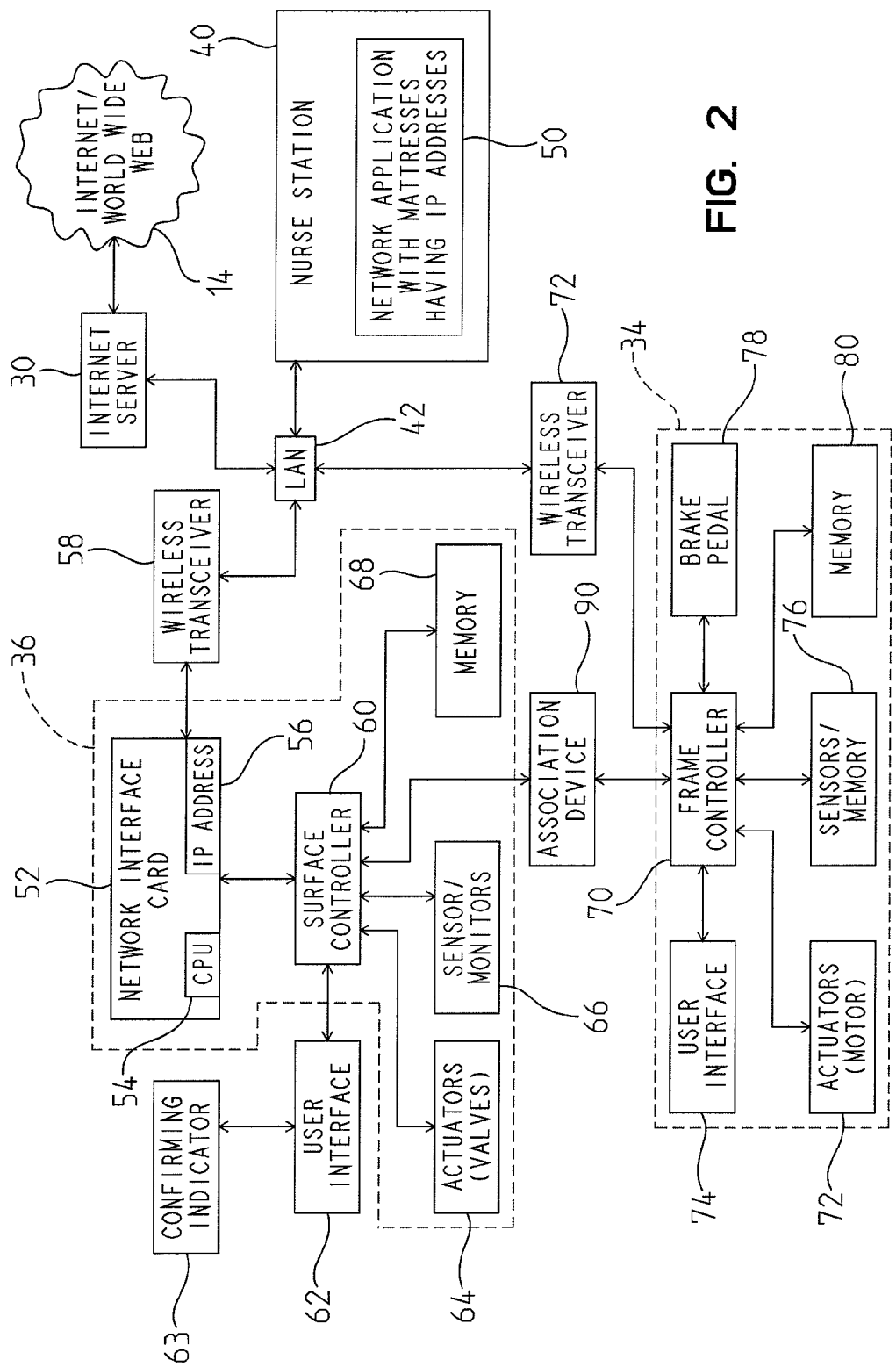
FIG. 2 illustrates a diagrammatic view of an information system of a healthcare facility coupled to the internet/worldwide web.

FIG. 2 illustrates more particularly the nurse station 40 and the various devices used to provide communication between the frame 34, the mattress 36, and the internet/worldwide web 14. As previously described, the healthcare facility 12 includes a local area network 42 which is coupled to a nurse station 40. The nurse station 40 includes a network application which is typically maintained and modified as necessary by an administrator.

The network application 50 of the present invention enables the administrator to assign each of the mattresses 36 with a unique identifier such as a unique IP address. The term IP address refers to an internet protocol (IP) address which is also known as a network address. The IP address can be assigned and changed in various ways, including being assigned and changed by a system administrator or by an authorized user having access to the network application 50. A fixed IP address can include a 32-bit (4-byte) binary number that uniquely identifies the mattress 36. Other electronic identifiers can also be used.

To uniquely identify each of the mattresses 36, a network interface device or card (NIC) 52 is incorporated into the mattress 36. The network interface card 52 is a known device which can be purchased from a variety of vendors. The network interface card 52 includes a central processing unit (CPU) 54 for manipulating data which is received by or transmitted by the network interface card over the local area network 42. The network interface card 52 also includes the assignable IP address 56. Communication over the local area network 42 can be accomplished by a wireless transceiver 58 which can communicate with the network interface card 52. The wireless transceiver 52 can either be incorporated into the network interface card 52 or can be a separate device as is understood by those skilled in the art. In addition, the wireless transceiver 58 can be incorporated either into the mattress 36, into the frame 34 or other components of the hospital bed. It is preferred, however, that the wireless transceiver be incorporated as a component of the mattress, such that when a mattress is moved from one location to another, the transceiver moves with the mattress.

In addition to the network interface card 52 located within the mattress 36, a surface controller 60 located within the mattress 36 is coupled to the network interface card 52. The surface controller 60 can include a variety of control functions for controlling the operation of the mattress. For instance, the mattress can include features such as percussion, vibration, turning, rotation, turn assist, as well as heating and cooling. A user interface 62 coupled to the surface controller 60 can be used to adjust the various control functions. The user interface 62 includes for instance, a touch screen or other manually activated buttons which enable a caregiver to control the various described functions. One or more confirming indicators 63 as described later herein can be included. Voice recognition can also be provided. The user interface 62 is typically incorporated into a control box which can be external to the mattress 36 but is coupled thereto by one or more control lines as is known by those skilled in the art. It is also possible to incorporate some, many, or all of the components of the control box into the mattress.

Upon selection of the desired functions through the user interface 62, one or more actuators or valves 64 respond accordingly to control the described features, such as percussion and/or vibration. In addition, one or more sensors and/or monitors 66 can be coupled to the surface controller 60 to provide sensed characteristics of the patient, the bed, or the interface between the patient and bed. For instance, the mattress 36 can include pressure sensors for determining patient pressure upon the mattress and send such information to the surface controller 60. The surface controller 60, which includes a central processing unit, can cause the actuators/valves to respond accordingly to address the sensed pressures based upon algorithms which can be located in a memory 68. The memory 68, not only can include algorithms for controlling the mattress 36, but can also be used to store data received from the actuators 64 and the sensors/monitors 66. The data stored in the memory 68 can then be accessed by the local area network 42 through the wireless transceiver 58.

The mattress 36 is supported by the frame 34. The frame 34 includes a frame controller 70 which includes a central processing unit to control the various functions of the frame. For instance, one or more actuators 72 such as a motor can be activated by the frame controller 70 upon entry of commands through a user interface 74. The user interface 74 can be included in a control pendant, a controller either coupled to or incorporated into a siderail, or other user interface devices which may be incorporated into the headboard, footboard, or other portions of the frame 34. The frame 34 also includes sensors/monitors 76 which can be used to monitor the operation of the actuators 72 or which can also be used to monitor the position and/or location of a patient being supported by the frame. In addition, the frame controller 70 can be coupled to the brake pedal 78 which can receive a signal from the brake pedal indicating the status thereof. Such a status signal can be communicated by the frame controller 70 to a wireless transceiver 72 which communicates with the local area network 42 to provide status information to the nurse station 40. While the wireless transceiver 72 is indicated as being distinct from the wireless transceiver 58, certain functions of the transceiver 72 can be shared by the transceiver 58. A memory 80 is coupled to the frame controller 70 and includes software having instructions for controlling the central processing unit. The memory 80 can also be used to store status information which is received from the actuators 72, the sensors 76 and user inputs through the user interface 74.

Each of the frames 34 can include an identifier, which can be unique, which can be communicated to the nurse call station 40 using a network interface unit and/or wireless interface unit.

Figure 3:
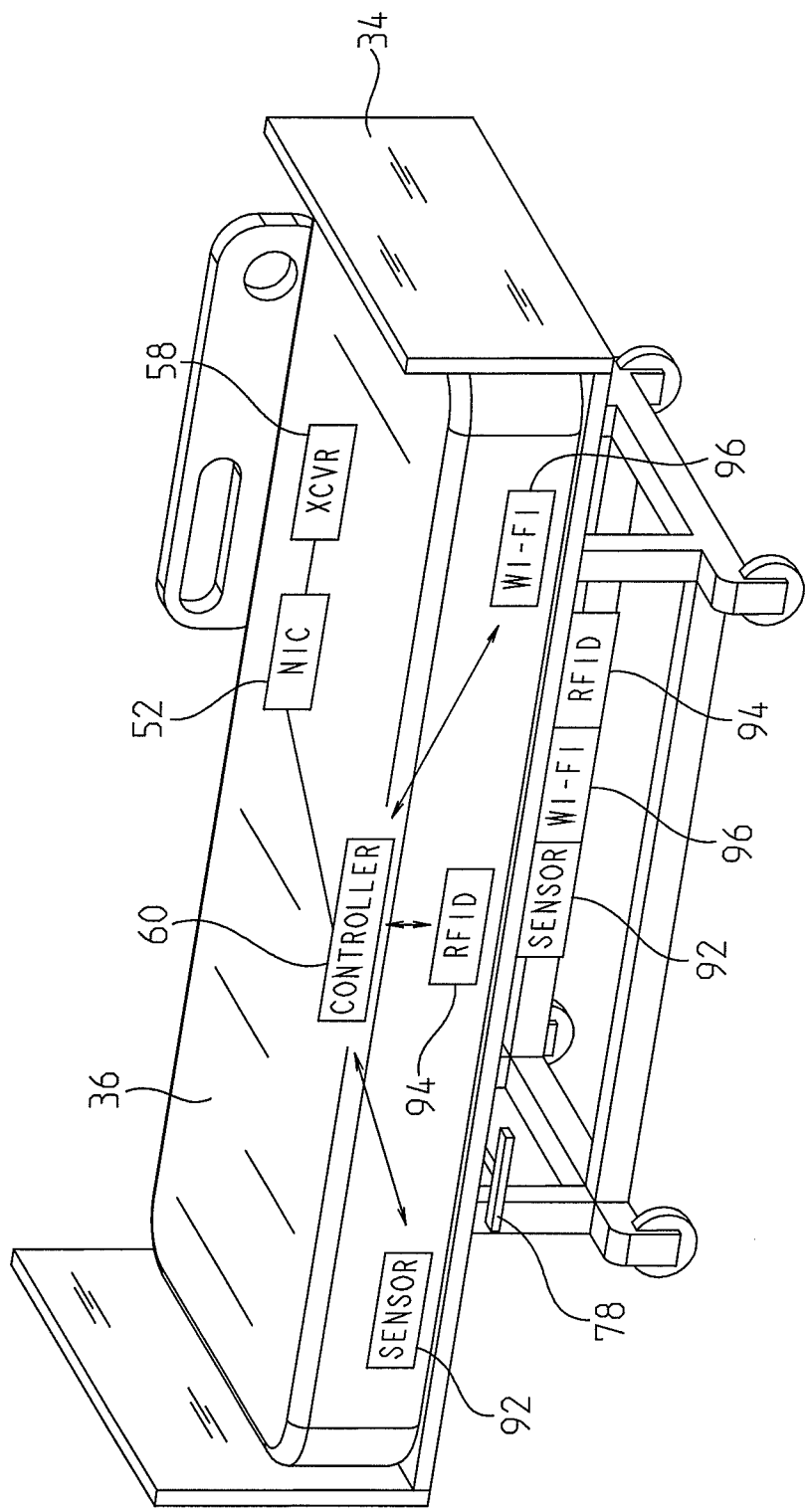
FIG. 3 illustrates a hospital bed of the present invention including a frame and a mattress having a unique identifier.

Once the mattress 36 is placed on the frame 34, an association device or a communicator 90 recognizes that a surface or support 36 has now been associated with the frame 34. The association device can reside on the mattress 36, on the frame 34, or portions thereof can be located on both the frame 34 and the mattress 36. For instance, as illustrated in FIG. 3, the association device can include a sensor 92, an RFID system 94, or a wi-fi system 96. For instance, the sensor 92 can include a magnetic sensor, such as a Hall effect transducer, wherein the Hall effect transducer provides a signal indicating the association of the mattress with the frame.

The surface can also be associated with the frame through a partially automatic system which includes an interactive response with or from a service technician or other installer. For instance, a wi-fi system 96 can be incorporated into the mattress 36. Upon toggling of the brake 78, a signal is sent from the brake to the frame controller 70 of FIG. 2. The controller 70 then provides a signal to the wi-fi system 96 for it to notify the controller of the mattress 36 that the brake has been set. Once the controller 60 has received the wi-fi signal, the controller 60 causes the transceiver 58 to transmit the identity of the mattress contained in the network interface card 52. In this way, setting or toggling of the brake can be used to indicate association of a uniquely identified mattress with a frame and/or a location. In another embodiment, an RFID reader 94 can be used to sense an RFID tag located on the mattress 36. Upon sensing the RFID tag, the RFID reader located on the frame 94 causes the surface controller 60 to transmit information through the wireless transceiver 58 indicating the unique identity of the mattress 36 contained in the IP address 56. The association device 90 can be incorporated as part of the controller.

Figure 4:
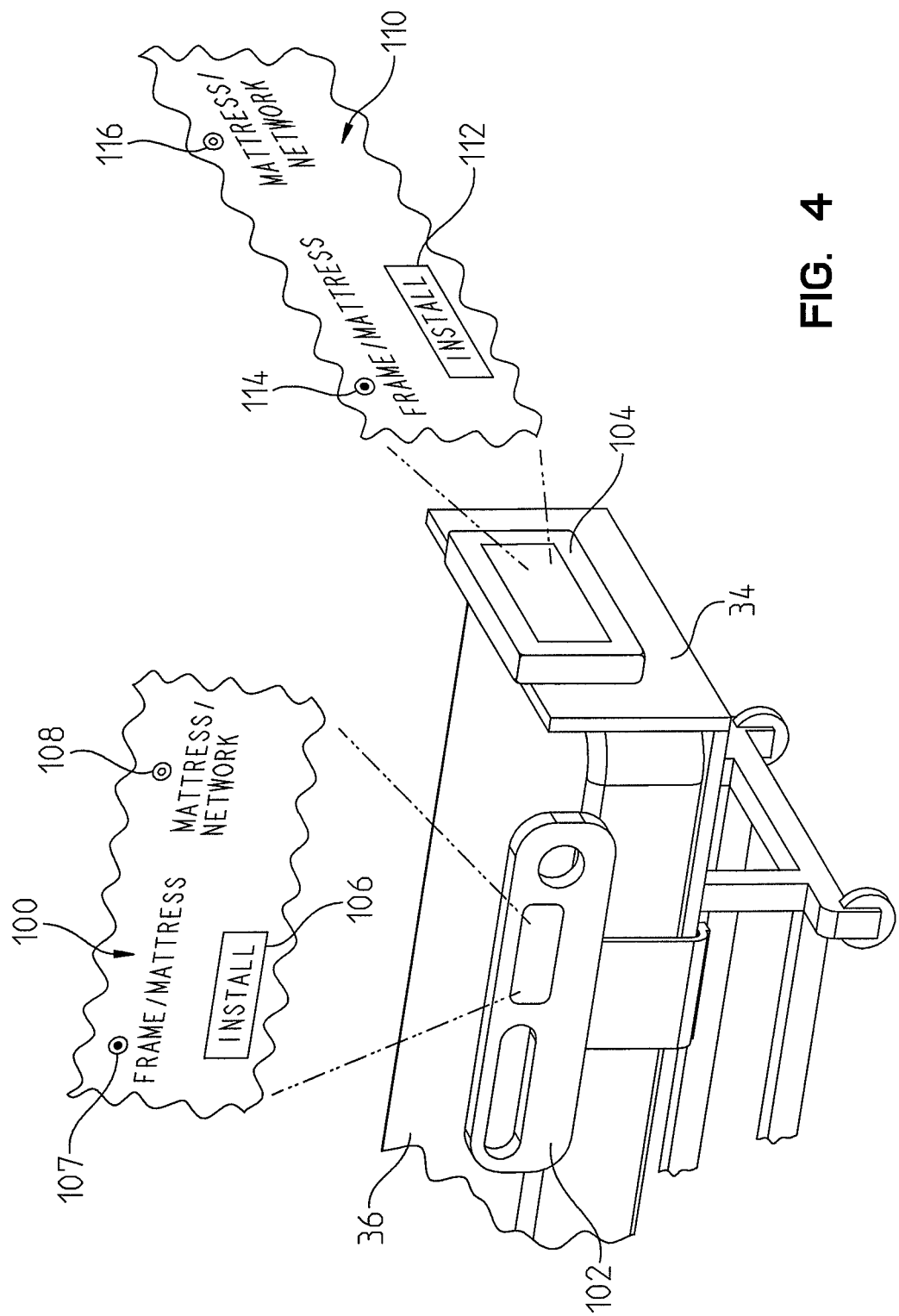
FIG. 4 illustrates a portion of a user interface located on a hospital bed to indicate the status of a mattress/frame combination with a mattress including the unique identifier.

As illustrated in FIG. 4, an install confirmation device 100 can indicate installation of a mattress to a frame and confirmation that the mattress has been properly recognized by the frame 34. The install confirmation device 100 can be incorporated in a siderail 102, in a control box 104, which is typically electrically and fluidically coupled to the mattress 36, or in the mattress itself. Once the mattress 36 has been placed on the frame 34, the installer or service technician presses an install button 106 located on the user interface device 100. Pressing the install button 106 transmits a signal from the frame controller 70 to the surface controller 60 through a communication device such as the wi-fi device 96. Once the signal is recognized by the surface controller 60, a frame/mattress indicator 107, or an illumination device, such as an incandescent light, an LED, or an audible indicator is activated. The frame/mattress indicator 107 indicates that the surface controller 60 has recognized a signal from the frame controller 70 indicating that the mattress 36 is now associated with the frame 34. In one embodiment, the surface controller can transmit the signal to the frame via the wi-fi device 96.

Once the surface controller 60 has received the signal from the frame controller 70, the surface controller 60, in combination with the network interface card 52, provides a signal, including the unique mattress IP address, which is transmitted by the wireless transceiver 58 to the local area network 42 and eventually to the nurse station 40. The nurse station 40 upon receipt of this information enters the unique identifier IP address to the network application used to indicate the location of the mattress. The IP address can be entered into a database automatically by the network application.

Once this information has been entered into the nurse station 40, the network application provides a signal from the nurse station 40 to the LAN 42 and back to the wireless transceiver 58. Such a signal causes the surface controller 60 to communicate with the frame controller 70 and to illuminate a mattress/network indicator 108. Other indicators are also possible as previously described.

It is not necessary to include the install button 106 in the interface 100 since the previously described sensor 92, RFID 94, and wi-fi device 96 can be used to transmit the necessary signal to the mattress to indicate that the frame and mattress have been associated as indicated by the indicator 106. In addition, it is not necessary to include both the indicator 106 and the indicator 108. It is within the scope of the present disclosure to include a single indicator which indicates that the mattress has been associated with the frame and that the mattress and its unique identifier have been recognized by the network.

An install/confirmation device 110 can also be incorporated into the mattress controller 104. The install/confirmation device 110 includes an install button 112, a frame/mattress indicator 114 and a mattress/network indicator 116. If either the frame/mattress indicator and/or mattress/network indicator does not illuminate, the installer can act accordingly. For instance, if the frame/mattress indicator 106 does not illuminate, the installer can contact the appropriate service technician who is familiar with the operation of the frame controller and its various related components and the surface controller and its various related components. The service technician can then diagnose the problem and make a repair or provide a replacement as necessary. However, if the frame/mattress indicator 114 does illuminate, but the mattress/network indicator 116 does not, then the installer can contact either a service technician familiar with the frame and mattress systems or can contact a service technician familiar with the network systems. Consequently, the use of a first and/or a second confirming indicator(s) can provide information useful for localizing a problem should one exist.

Figure 5:
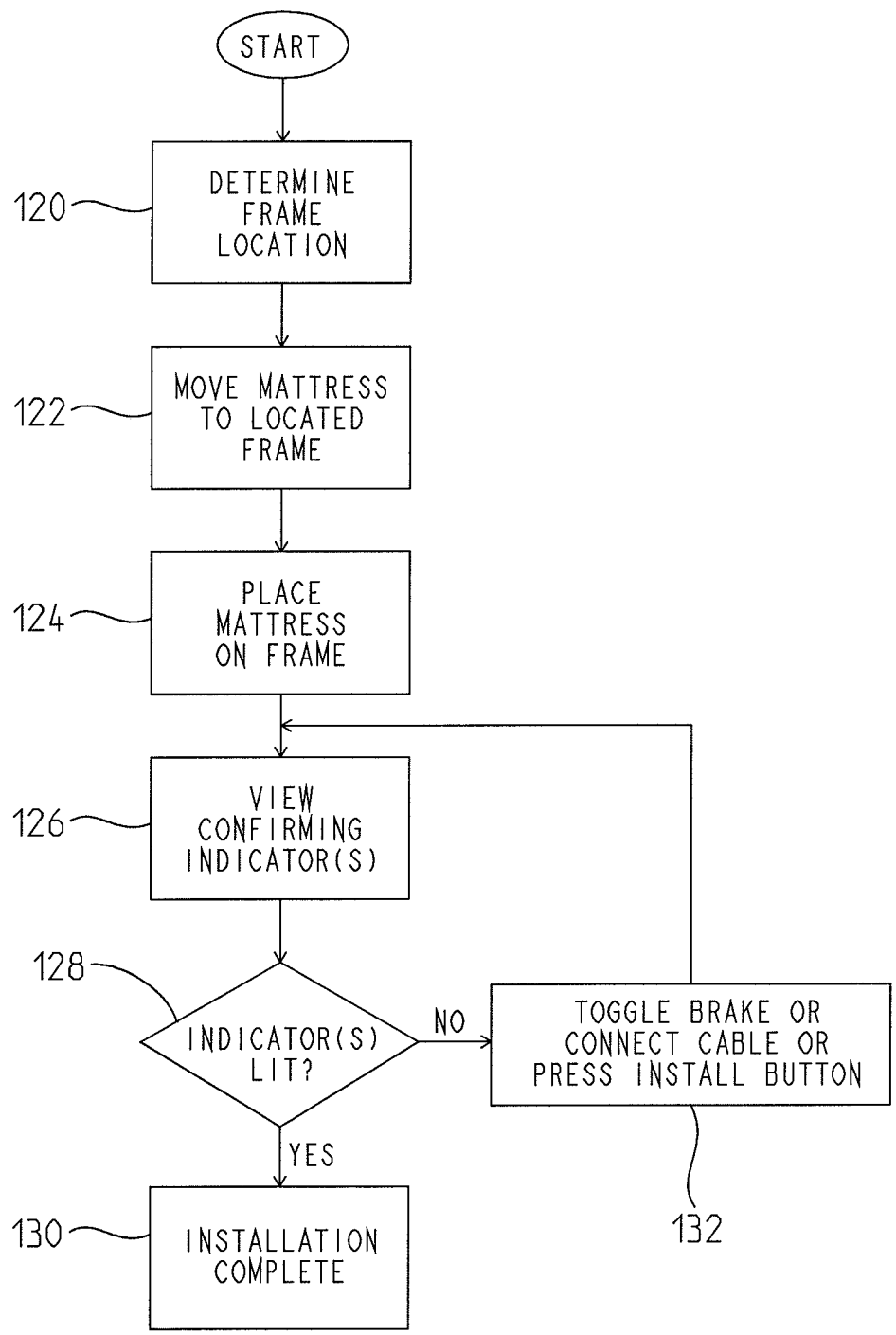
FIG. 5 illustrates a block diagram including the steps of installing a mattress having a unique identifier on a frame.

FIG. 5 illustrates one embodiment of a flow chart which can be used by an installer or service technician to complete installation of the mattress to the frame. For a service technician to mate a mattress with a frame, the service technician first determines the frame location at step 120. This information can typically be accessed through the nurse station 40. Once the frame location has been determined, the service technician takes a selected mattress from the determined location and moves the mattress to the destination or to the located frame at step 122. At step 124 the mattress is placed on the frame. At step 126 the service technician views the confirming indicator or indicators. Because it is possible that the mattress/frame confirmation system can be totally automatic, step 128 includes determining whether both indicators or a single indicator are illuminated. If the indicator is illuminated at step 128, then at step 130 it is determined that the installation is complete. If, however, the indicator is not illuminated at step 128, the service technician at step 132 will toggle a brake or connect a cable or press the install button to begin the process of associating the mattress with the frame. Once the actions have been completed at step 132, the service technician again views the confirming indicators at step 126. Depending on the indicators being illuminated or not illuminated, it is determined that the installation is complete at step 130. Of course, if the indicators never illuminate, an appropriate repair technician can be called.

Once the mattress has been associated with the frame and the unique IP address of the mattress has been transmitted to the nurse station 40, the mattress identification information can be accessed by a caregiver or nurse at the nurse station. Because the system includes the use of the internet/world wide web 14, a remotely located user can also access the information through a computer system such as computer system 16. It is therefore possible for an individual to view information when located externally to the healthcare group 10, such as at home.

At the nurse station 40, or other location, the caregiver can view a variety of data which can be associated with a particular mattress. A user application residing at the nurse station 40 can include a number of user interface screens such as those illustrated in FIG. 6A through FIG. 6E. In one embodiment of the present invention, a web browser is used to display the user interface screens.

A first user interface screen 140 includes information relating to a patient, a mattress, and a location of the mattress. Because it is possible to uniquely identify the mattress and the location thereof, the patient currently on the mattress can also be linked or associated with the identified mattress. Consequently, the user interface screen 140 of FIG. 6A can provide cross-referenced information and/or data of the patient and the patient's mattress. For instance, if the caregiver is interested in determining what type of mattress a particular patient is using, the caregiver can select alphabetically by a patient's last name the desired information. If the caregiver wishes to determine the type of mattress a patient having the name J. Jones is lying on, the caregiver would select the F-J column of the user interface 140. Upon selection of the F-J column, the patients having last names F through J would appear on a screen 142 as illustrated in FIG. 6B. Patients having last names beginning with the letters F through J would be illustrated on the patient screen 142, which in this example is only illustrated to show the selected patient J. Jones.

The unique mattress identifier can provide a variety of useful information to the caregiver. For instance, a healthcare unit 32, such as an intensive care unit (ICU), may have a number of mattresses. The network administrator setting up the system can use the unique identifiers of each mattress to provide a mattress ID (identifier) for use in this particular screen. For instance, if there are ten mattresses in the ICU, they could be given mattress ID's ICU ONE through ICU TEN, since IP addresses when displayed may provide only the numbers. Consequently, the mattress ID, ICU ONE, is not unlike a domain name, since web addresses can be both the actual IP address and a domain name associated therewith. A third column STATUS, in the screen 142 can include the status of the mattress. If the mattress has indeed been associated with a frame, then the status "IN USE" can be displayed. If a mattress, however, has not been associated with a frame, the status could be indicated as "NOT IN USE." A fourth column, LOCATION, indicates the location of the mattress which has now been associated with a particular frame. In this case, the location is indicated as ICU-Third Floor.

Because the mattress has a unique identifier and that identifier can indicate the type of mattress being used, a column indicating TYPE will display the type of mattress. For instance, the type can be generalized such that there are a limited number of types which might include a foam mattress, an air mattress, and a therapy mattress. The types can be respectively identified at TYPE 1, TYPE 2, or TYPE 3. Because the type of mattress is known, a FEATURES column can indicate the features which are included for that type of mattress. For instance, the features list could say "FOAM" or as is illustrated, the features list can indicate that the mattress has "MULTIPLE" features. It is within the scope of the present invention for the caregiver to move the cursor of the mouse over the word "FEATURES." A drop down menu, provided by the application software, can automatically be displayed indicating each of the features present in that particular mattress.

Figure 6A:
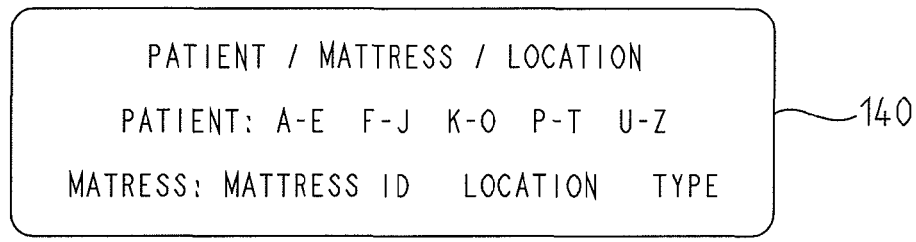
FIGS. 6A-6E illustrates a plurality of user interface screens located on the information system of the present invention.
Figure 6B:
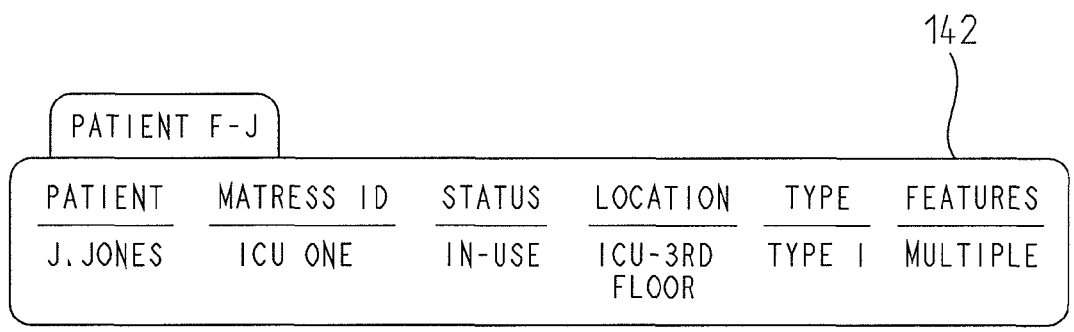
Figure 6C:
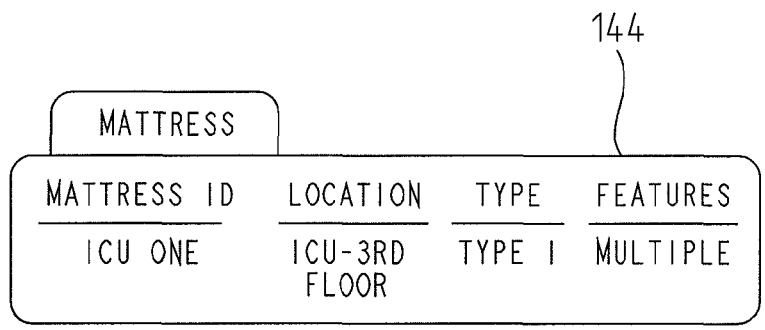

Should the caregiver viewing user interface screen 140 instead desire to view a particular uniquely identified mattress, the caregiver can select the "MATTRESS" selector in FIG. 6A to access the user interface screen 144 of FIG. 6C. In this case, a number of mattress ID's would appear, only one of which is shown. The mattress ID of FIG. 6C is indicated as being ICU ONE. The location, type, and features of such a mattress are also provided.

Figure 6D:
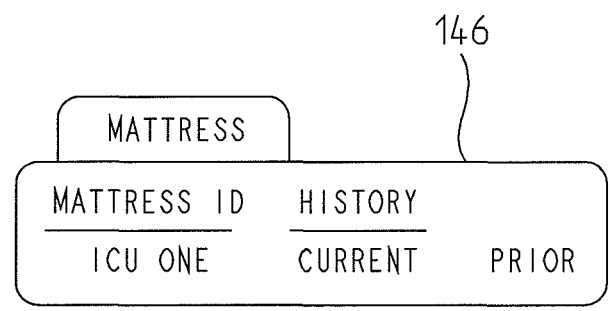
Figure 6E:
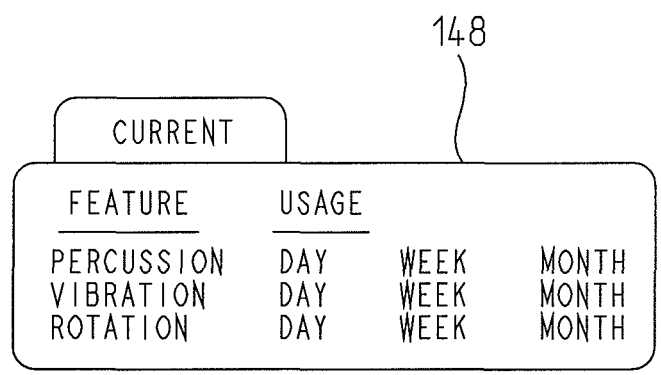

As illustrated in FIG. 6D, it is also possible to access the history or the use of a mattress over a period of time. For instance, since the mattress 36, as illustrated in FIG. 2, includes a memory 68, the memory can be used to store historical and/or current status data. If a caregiver at the user interface screen 146 selects the current history of the ICU ONE mattress, a user interface screen 148 as illustrated in FIG. 6E is provided. Because the ICU ONE mattress includes multiple features, the multiple features are displayed, which in this case are percussion, vibration and rotation. Also since the mattress ICU ONE is associated with a particular patient, it is possible to determine which features have been used over a period of time. The usage can be displayed in any number of time periods, but it is possible to indicate the usage over a day, over a week, over a month, or some other period of time. If the current patient has not been associated with this particular mattress for more than a week, the information displayed under the month would indicate such use as being no usage.

If, however, the caregiver had selected the history of "PRIOR" at the user interface screen 146 of FIG. 6D, all of the prior history of this particular mattress can be displayed. Consequently, for this particular mattress, the amount of time the mattress provided percussion therapy, the amount of time the mattress provided vibration therapy, and the amount of time the mattress provided rotation therapy, could be accessed. Such information can be useful to determine whether or not this particular type of mattress is appropriate for a location within a particular location or unit of a healthcare facility. For instance, if the percussion and vibration use is minimal, it may indicate that a different type of mattress should be used in this particular location. In addition, such information can also be useful to service personnel to indicate the amount of time a mattress can be used before requiring service.

While an exemplary embodiment incorporating the principles of the present invention has been disclosed hereinabove, the present invention is not limited to the disclosed embodiments. Instead, this application is intended to cover any variations, uses, or adaptations of the invention using its general principles. Further, this application is intended to cover such departures from the present disclosure as come within known or customary practice in the art to which this invention pertains and which fall within the limits and scope of the appended claims.

What is claimed is:

1. A mattress for use in a healthcare facility having a communication system and a plurality of bed frames, the mattress comprising:
   a support member;
   a unique electronic identifier, associated with the mattress, to uniquely identify the mattress; and
   a transceiver, associated with the mattress and operably coupled to the communication system, to transmit the unique electronic identifier over the communication system;
   a bed frame transceiver associated with a bed frame from the plurality of bed frames;
   an install-confirming device comprising a user input button that is used to confirm placement of the mattress on one of the bed frames of the plurality of bed frames;
   a communications network coupled to the transceiver, the bed frame transceiver, and the install-confirming device, the communications network used to communicate data between the transceiver, the bed frame transceiver, and the install-confirming device;
   a first visual indicator to indicate whether the mattress is successfully associated with one of the bed frames of the plurality of bed frames, the first visual indicator coupled to the install-confirming device;
   a second visual indicator to indicate whether the transceiver associated with the mattress is successfully communicating with the communication system of the healthcare facility, the second visual indicator coupled to the install-confirming device, the second visual indicator becoming enabled when the bed frame transceiver receives, via the communications network, a confirmation signal from the communication system of the healthcare facility, the bed frame transceiver receiving the confirmation signal and causing the bed frame transceiver to enable the second visual indicator; and
   a controller coupled to the transceiver and the install-confirming device, the controller receiving a signal from the user input button to confirm that the mattress is placed on one of the bed frames of the plurality of bed frames, to activating the first visual indicator in response to determining a successful association, and activating the second visual indicator in response to determining successful communication with the communication system of the healthcare facility.

2. The mattress of claim 1, further comprising a network interface device operably coupled to the transceiver, the network interface device adapted to store the unique electronic identifier.

3. The mattress of claim 2, further comprising an association device, coupled to the network interface device, the association device adapted to receive a signal indicative of an association with one of the plurality of bed frames.

4. The mattress of claim 3, wherein the transceiver comprises a wireless transceiver.

5. The mattress of claim 4, wherein the wireless transceiver comprises a part of the network interface device.

6. A method of determining the location of a mattress within a healthcare facility having a communication system, a plurality of bed frames, and a plurality of mattresses, comprising the steps of:
   providing a plurality of mattresses each having a unique identifier stored in an electronic device;
   placing one of the uniquely identified mattresses on one of the plurality of bed frames;
   confirming placement of one of the uniquely identified mattresses on the one of the plurality of bed frames using an install-confirming device which is coupled to one of the plurality of bed frames and sends a signal to a controller to confirm that the mattress is placed on one of the bed frames of the plurality of bed frames;
   determining whether one of the uniquely identified mattresses is successfully associated with one of the plurality of bed frames by viewing a first visual indicator coupled to the install-confirming device, the first visual indicator being activated by the controller in response to determining a successful association;
   determining whether one of the uniquely identified mattresses is successfully communicating with the communication system of the healthcare facility by viewing a second visual indicator coupled to the install-confirming device, the second visual indicator being activated by the controller in response to determining successful communication with the communication system of the healthcare facility; and
   sending the unique identifier assigned to one of the uniquely identified mattresses over the communication system.

7. The method of claim 6, wherein the confirming step comprises confirming placement of the one of the uniquely identified mattresses by actuating a device located on the one of the plurality of frames.

8. The method of claim 7, wherein the device located on the one of the plurality of frames comprises a brake pedal.

9. The method of claim 8, wherein the device located on the one of the plurality of frames comprises a user activated device.

10. The method of claim 9, wherein the user activated button comprises a mechanical button.

11. The method of claim 9, wherein the user activated button comprises a touch screen display.

12. A system for use in a healthcare facility comprising:
   a communication system;
   a transceiver associated with a mattress among a plurality of mattresses;
   a plurality of uniquely identified mattresses, each of the uniquely identified mattresses including a unique electronic identifier;
   a plurality of bed frames;
   a bed frame transceiver associated with a bed frame from the plurality of bed frames;
   a plurality of install-confirming devices, each install-confirming device operable to receive user input to confirm the placement of one of the plurality of mattresses on one of the plurality of bed frames;
   a communications network coupled to the transceiver, the bed frame transceiver, and an install-confirming device from the plurality of install-confirmation devices, the communications network used to communicate data between the transceiver, the bed frame transceiver, and the install-confirming device;

a first visual indicator coupled to each one of the plurality of install-confirming devices to indicate whether each bed frame is successfully associated with a respective mattress of the plurality of mattresses;

a second visual indicator coupled to each one of the plurality of install-confirming devices to indicate whether the respective transceiver associated with the mattress is successfully communicating with the communication system of the healthcare facility, the second visual indicator becoming enabled when the bed frame transceiver receives, via the communications network, a confirmation signal from the communication system of the healthcare facility, the bed frame transceiver receiving the confirmation signal and causing the bed frame transceiver to enable the second visual indicator; and a plurality of controllers, each controller of bed each controller coupled to one of the plurality of install-confirming devices and receiving a signal from one of the plurality of install-confirming devices to confirm that one of the mattresses is placed on one of the plurality of bed frames, activating the first visual indicator in response to determining a successful association, and activating the second visual indicator in response to determining successful communication with the communication system.

13. The system of claim 12, wherein each of the plurality of uniquely identified mattresses comprise a support member and a transceiver, associated with the mattress, the transceiver being operably coupled to the communication system, to transmit the unique electronic identifier over the communication system.

14. The system of claim 13, wherein the unique electronic identifier comprises an interne protocol address.

15. The system of claim 14, wherein each of the uniquely identified mattresses comprise a network interface device operably coupled to the transceiver, the network interface device adapted to store the unique electronic identifier.

16. The system of claim 15, wherein the transceiver comprises a wireless transceiver.

17. The system of claim 16, wherein the wireless transceiver comprises a part of the network interface device.

18. The system of claim 13, further comprising a computing device coupled to the communication system to receive and store the unique electronic identifiers from the plurality of uniquely identified mattresses.

19. The system of claim 13, wherein the computing device provides an interface to present information regarding the plurality of uniquely identified mattresses.

20. The system of claim 13, wherein the interface presents information that identifies each mattress of the plurality of uniquely identified mattresses and that identifies a patient assigned to each mattress of the plurality of uniquely identified mattresses.

21. The system of claim 13, wherein the interface presents information that identifies each mattress of the plurality of uniquely identified mattresses and that identifies a location of each mattress in the healthcare facility.

22. The system of claim 13, wherein the interface presents information that identifies each mattress of the plurality of uniquely identified mattresses and that identifies a type for each mattress.

23. The system of claim 13, wherein the interface presents information that identifies each mattress of the plurality of uniquely identified mattresses and that identifies features provided by each mattress.

24. The system of claim 13, wherein the interface presents information that identifies each mattress of the plurality of uniquely identified mattresses and that identifies a history of use for each mattress.

* * * * *